(12) United States Patent
Krotz et al.

(10) Patent No.: US 9,147,038 B2
(45) Date of Patent: Sep. 29, 2015

(54) METHOD FOR CONFIGURING AT LEAST ONE COMMUNICATIONS LINK FOR TRANSMITTING MEDICAL IMAGE DATASETS AND SYSTEM FOR MANAGING AND/OR PROCESSING MEDICAL IMAGE DATASETS

(75) Inventors: Dieter Krotz, Erlangen (DE); Björn Nolte, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 275 days.

(21) Appl. No.: 13/013,855

(22) Filed: Jan. 26, 2011

(65) Prior Publication Data
US 2011/0213889 A1 Sep. 1, 2011

(30) Foreign Application Priority Data
Feb. 26, 2010 (DE) .......................... 10 2010 009 463

(51) Int. Cl.
| G06F 15/16 | (2006.01) |
| G06F 19/00 | (2011.01) |
| G06F 15/177 | (2006.01) |
| H04L 12/24 | (2006.01) |
| H04L 29/08 | (2006.01) |

(52) U.S. Cl.
CPC ............... *G06F 19/321* (2013.01); *H04L 41/12* (2013.01); *H04L 67/12* (2013.01)

(58) Field of Classification Search
CPC ........ G06F 19/321; H04L 41/12; H04L 67/12
USPC ............................. 709/227, 228, 229; 370/332
See application file for complete search history.

(56) References Cited

U.S. PATENT DOCUMENTS

| 2004/0100949 | A1* | 5/2004 | Bennett ......................... 370/384 |
| 2006/0291385 | A1* | 12/2006 | Yang ............................. 370/229 |
| 2008/0056212 | A1* | 3/2008 | Karaoguz et al. ............. 370/338 |
| 2008/0279183 | A1* | 11/2008 | Wiley et al. .................... 370/389 |
| 2009/0091765 | A1 | 4/2009 | Chow et al. |
| 2009/0129653 | A1* | 5/2009 | DeHority et al. ............. 382/132 |
| 2009/0190558 | A1* | 7/2009 | Strutt et al. ................... 370/332 |
| 2010/0091659 | A1* | 4/2010 | O'Hanlon et al. ............ 370/241 |
| 2010/0097631 | A1* | 4/2010 | DeRoller et al. ............. 358/1.15 |

(Continued)

OTHER PUBLICATIONS

Gohel, N. R. et al; "Evaluation of Multi-Megabit Networks for Medical Information Delivery"; Medical Imaging, International Society for Optics and Photonics; SPIE; vol. 2711; pp. 560-568; DOI: 10.1117/12.239293; 1996.

(Continued)

*Primary Examiner* — Brian J Gillis
*Assistant Examiner* — Juan C Turriate Gastulo
(74) *Attorney, Agent, or Firm* — Harness, Dickey & Pierce, P.L.C.

(57) ABSTRACT

A method is disclosed for configuring at least one communications link for transmitting medical image datasets by means of a special transmission protocol, in particular the DICOM protocol, from a first computing device to at least one second computing device, in particular a plurality of different second computing devices. In at least one embodiment, the transmission performance is determined automatically at the first computing device for a plurality of sets of configuration parameters of the communications link and the set of configuration parameters having the best transmission performance is selected for the configuration.

12 Claims, 1 Drawing Sheet

(56) References Cited

U.S. PATENT DOCUMENTS

2010/0138523 A1* 6/2010 Urness et al. ............ 709/222
2011/0044356 A1* 2/2011 Hadad et al. ............ 370/480
2011/0145373 A1* 6/2011 Awad et al. ............ 709/220

OTHER PUBLICATIONS

German Office Action dated Feb. 4, 2014 in corresponding Application No. 10 2010 009 463.3.

* cited by examiner

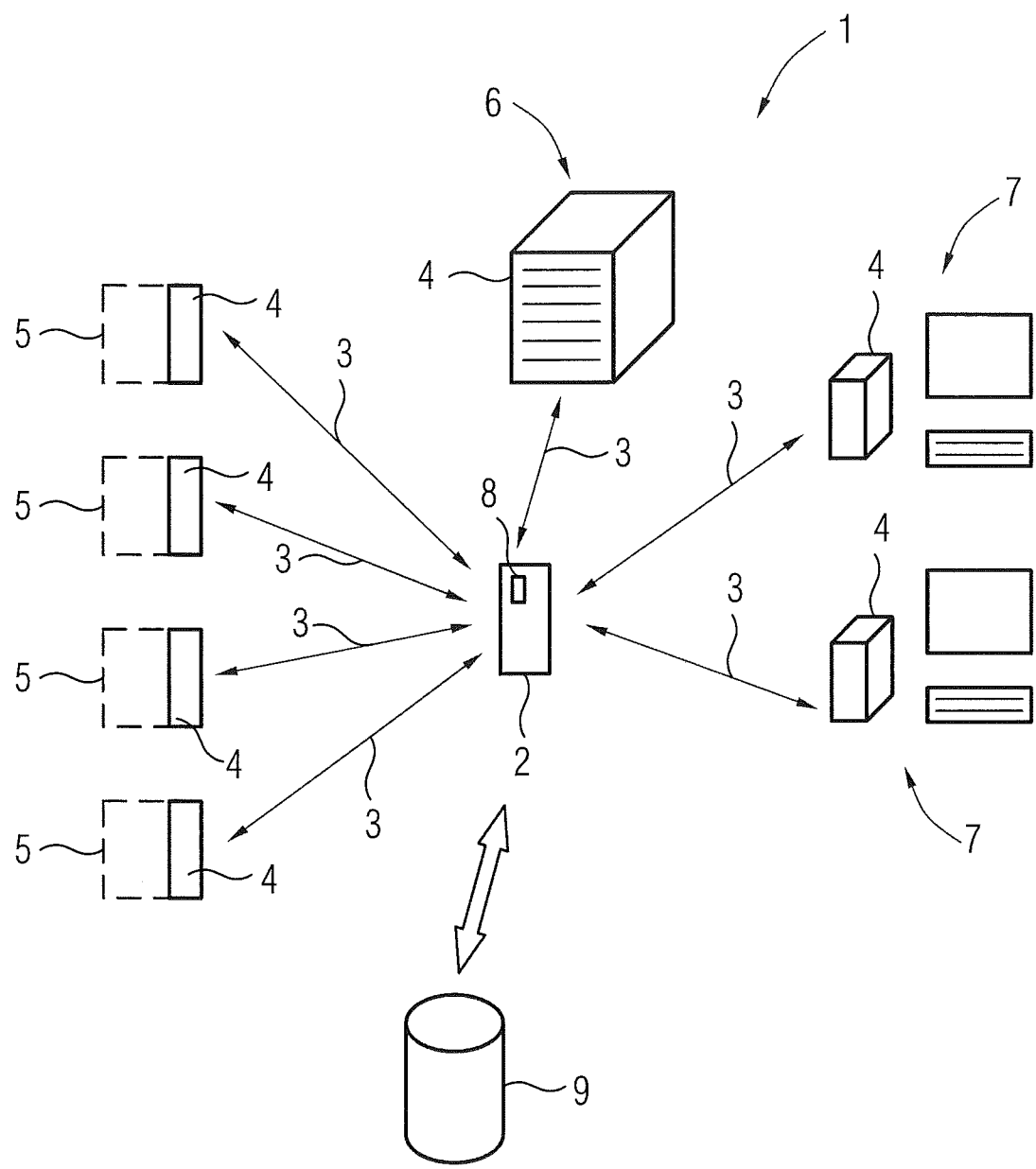

METHOD FOR CONFIGURING AT LEAST ONE COMMUNICATIONS LINK FOR TRANSMITTING MEDICAL IMAGE DATASETS AND SYSTEM FOR MANAGING AND/OR PROCESSING MEDICAL IMAGE DATASETS

The present application hereby claims priority under 35 U.S.C. §119 on German patent application number DE 10 2010 009 463.3 filed Feb. 26, 2010, the entire contents of which are hereby incorporated herein by reference.

FIELD

At least one embodiment of the invention generally relates to a method for configuring at least one communications link for the purpose of transmitting medical image datasets by way of a special transmission protocol, in particular the DICOM protocol, from a first computing device to at least one second computing device, in particular a plurality of different second computing devices, as well as to an associated system for managing and/or processing medical image datasets by means of a plurality of computing devices.

BACKGROUND

With the continuing development of medical imaging technologies, the file sizes of recorded image datasets are becoming larger and larger and the number of recorded image datasets is increasing all the time. For archiving, storage and/or diagnostic purposes it is necessary to transport said image datasets, comprising several hundred images of a series of an examination, for example, via communications links from one computing device to another computing device. The term "computing device", in the context of the present application, is to be understood in a broad sense, encompassing both communication-capable control devices and conventional desktop computers for example.

The DICOM (digital imaging and communications in medicine) standard has meanwhile become widely established in the medical domain as a standard for the file formats and also for the data transmission. It is therefore standard practice to transmit image datasets by means of the DICOM transmission protocol from a first computing device to a second computing device. Of course, other transmission protocols, possibly even proprietary transmission protocols, tailored to the special format and size of the image datasets are also known. The DICOM protocol and where applicable other similar transmission protocols are geared to the specific needs arising for the transmission of medical image datasets.

There is, however, a problem in that the communications link itself is not optimized for the specific profile of medical data that is to be transmitted between two computing devices, which means that it is not possible to achieve an optimal transmission performance. This is particularly relevant since for specific communication parameters the transmission performance is also dependent on the type of target system or, as the case may be, target computing device. Medical systems having a plurality of computing devices that are used for managing and/or processing images, for example radiology information systems (RIS) or hospital information systems (HIS), are in this case frequently highly heterogeneous systems that comprise computing devices of the most disparate types and from the widest variety of manufacturers, for example in imaging devices for different modalities from different manufacturers, but also in terms of an archive server (PACS), for example. It can happen, for example, that a first computing device is embodied for setting up communications links for the purpose of transmitting medical image datasets to between three and thirty second computing devices, all of which can have different specifications. An example of a possible system architecture can be found in US 2009/0091765 A1, the entire contents of which are hereby incorporated herein by reference.

These days it is generally accepted practice to use a standard configuration for all communications links to and from a computing device. This configuration is mostly inherited as a manufacturer setup. It is, however, also known to have the configuration modified by a service technician in a complicated and time-consuming manual procedure. Ultimately, however, what one is left with in most cases is a suboptimal configuration which does not permit optimum transmission performance and consequently slows down the data transmission too much and ties up I/O resources of the computing devices.

SUMMARY

At least one embodiment of the invention therefore discloses a method for configuring communications links which permits an optimal calibration for each communications link, in particular in heterogeneous systems in which communications links must be set up to second computing devices having different specifications.

In at least one embodiment, the transmission performance is determined automatically at the first computing device for a plurality of sets of configuration parameters of the communications link and the set of configuration parameters having the best transmission performance is selected for the configuration.

An automatic configuration of at least one of the communications links, in particular of all of the communications links, is therefore provided in the method according to at least one embodiment of the invention. Toward that end test measurements of the transmission performance are taken for specific values of configuration parameters that influence the transmission performance; these entail, for example, transmitting a predefined dataset or predefined data packet that simulates the medical data back and forth by way of the transmission protocol, i.e. in particular the DICOM protocol.

Examples of parameters that can be considered for the purpose of determining the transmission performance are the transmission rate, the utilization of network capacity, resources of the transmitting and receiving computing device, and/or the transmission time, although other measurement values can also be included. Such measurement values can then be considered weighted, for example, in order to determine a value for the transmission performance. In this case the weighting can indicate how much value is placed on certain performance characteristics, whether, for example, it is more important to minimize utilization of the resources of the first computing device or to achieve a particularly high transmission rate. The set of configuration parameters that has the best transmission performance according to the measurements is then used for configuring the communications link and consequently stored in the first computing device for said communications link. If second computing devices with matching specifications are present, the results can also be applied to other communications links without the necessity of performing further measurements.

These functionalities can be realized, for example, by way of a program means, i.e. a software utility for example, which where necessary checks which second computing devices are provided for communication with the first computing device and then assumes the optimal configuration of the corresponding communications links.

Let it also be noted at this juncture that it will generally be provided that the configuration parameters will be optimized for both communication directions, i.e. both for the sending and for the receiving of medical image datasets; in individual cases it may also be expedient to perform the automatic optimization and configuration for one communication direction only.

In this way, at least one embodiment of the present invention accordingly provides a tool that permits a fully automatic improvement of the transmission performance for one or more, in particular all, communications links from a first computing device to a second computing device with regard to the medical data that is to be transported. This configuration is performed in particular without any user intervention and specifically for the corresponding second computing devices, of which 3-30 can be provided, for example. Thus, it is possible without significant expenditure of time and effort to improve the overall performance of a system of computing devices in which large volumes of data in the form of medical data must be transmitted on a regular basis, for which purpose a specific transmission protocol, in particular the DICOM protocol, is used. It should be pointed out that in the following description most of the examples are discussed with reference to the DICOM protocol, though it goes without saying that other protocols, proprietary protocols for example, are also conceivable.

Beneficially, the configuration can be performed for at least one communications link, in particular all of the communications links, at the time of installation of the first computing device. In this case the method according to at least one embodiment of the invention therefore constitutes that part of an installation process in which initially it can be specified, for example, with which second computing devices the newly installed first computing device is to communicate. Thereafter it is possible, as described, by using a software utility for example, to perform the configuration for the communications links, in particular all of the configuration links, with the aid of the method according to the invention. Furthermore this process can also be automated, which means that it is integrated fully automatically in the installation process without operator interaction. Let it also be noted at this juncture that not every communications link to a second computing device has to be configured or calibrated via the aforesaid measurements, but that it is also conceivable, as will be explained in more detail below, to make use of previously determined sets of communication parameters for known second computing devices.

In a further advantageous embodiment it can be provided that when a second computing device with which the first computing device is to communicate is added, the corresponding computing device will be configured automatically, where appropriate following confirmation by a user, and/or an automatic reconfiguration of a communications link will be initiated by a user, in particular by actuating a control element. It can therefore be provided that whenever a new second computing device is installed in the overall system, for example in the context of the installation of a new imaging device, a configuration of the communications link between the corresponding first computing devices and the new second computing device will be performed immediately and automatically or semiautomatically. For example, it can be provided that a user is presented with a dialog in which he or she is asked whether the communications device associated with the newly added and configured second computing device is now to be configured automatically for optimized performance. Following confirmation the most suitable set of configuration parameters can be determined.

It is, of course, also conceivable for a reconfiguration to be initiated at any time by a user. For that purpose a corresponding control element, for example, can be provided on the first computing device, said control element being assigned to the corresponding communications link or, as the case may be, corresponding second computing device in a general configuration utility, for example. A button "Recalibrate" can be provided, for example. Let it also be noted at this juncture that in principle it can always be provided that a manual configuration, which is to say a manual setting of the configuration parameters by a user, can also be permitted. This can prove useful, for example, when no optimization in respect of the transmission of medical image datasets is required, but essentially only limited resources are to be made available for this purpose, since the first computing device needs these resources for other tasks or the like. Let it be pointed out once again, however, that such objectives can also be expressed in a weighting of measurement values contributing toward the transmission performance.

In a particularly advantageous embodiment of the present invention it can be provided that a selected set of configuration parameters is stored in a database together with the type of the second computing device and/or equipment level data of the second computing device. Whenever an optimal configuration parameter set has been found for a specific second computing device, it can therefore be provided that this result is stored in a database. A database of said kind can be provided, for example, at a manufacturer facility or also in an internet portal. Such a database can then contain sets of configuration parameters for X-ray equipment of a specific type, other imaging equipment of a specific type, specific archive system computers and the like. The data of such a database can then be used, for example, to simplify subsequent configuration processes. Thus, it can be provided that the set of configuration parameters stored in the database can be retrieved and used for configuring a communications link to a second computing device that in terms of type and/or equipment level data matches a second computing device that is stored in the database. It is therefore possible to access the database in order to use the results of already performed measurements and configuration processes stored there for further configuration processes as well. While it can happen in the ideal case that the configuration parameter set from the database can be reused directly, there can also be cases in which said equipment level dataset is used as a starting point for further measurements aimed at improving the configuration even further.

At least one packet size, in particular a TCP/IP packet size and/or a DICOM PDU, and/or parameters for coordinating a plurality of network cards of the first device and/or a parameter describing bulk and/or burst modes can be used as configuration parameters. In TCP/IP the relevant packet sizes are mainly the send packet size and the receive packet size. Similarly, there are also packet sizes in the DICOM protocol, namely the so-called PDUs (DICOM Processing Data Units). A good configuration is possible already with the TCP/IP packet sizes and the DICOM PDUs, i.e. with four parameters. However, it is also conceivable to include further parameters, for example parameters for coordinating a plurality of network cards of the first computing device (often also referred to as "teaming"; a plurality of network cards cooperate within the framework of a single data transmission). Finally, parameters that describe bulk and/or burst modes are also conceivable. This list of possible parameters is obviously not exhaustive; other parameters that have an impact on the transmission performance can also be included in the consideration and be optimized automatically in this regard.

An optimization method can beneficially be used for determining a set of configuration parameters having the best transmission performance. Optimization methods that are optimized in a parameter space in terms of a cost function which in this case describes the conditions for the transmission performance are essentially widely known. Different types of optimization methods can be used in this case, with both simple optimization methods and also rather complex procedures being conceivable. Thus, for example, it can be provided that a matrix is used, each column vector of which having in particular monotonously increasing entries contains values for a configuration parameter, with measurements being performed for the purpose of determining the transmission performance for a plurality of, in particular all, parameter combinations. For example, if the four packet sizes already discussed above are considered as configuration parameters, seven to eight predetermined, discrete values can be provided per configuration parameter in the matrix and a measurement performed without great expenditure in terms of time for each of these combinations. The measurement that demonstrates the best transmission performance then consequently also has the most suitable set of configuration parameters. However, other approaches are also conceivable in this case; for example, greater increments can be selected initially, in particular in the case of more finely subdivided predefined values for the configuration parameters, in order to discover in which range the optimum approximately lies, so that further measurements can then be performed in said range. However, it should be pointed out once again that in addition to such matrices having discrete possible values for the configuration parameters it is of course also possible to use an optimization method which considers the configuration parameters essentially continuously.

In addition to the method, at least one embodiment of the invention also relates to a system for managing and/or processing medical image datasets by means of a plurality of computing devices which are characterized in that at least one communications link for transmitting medical image datasets by means of a special transmission protocol, in particular the DICOM protocol, from a first computing device to at least one second computing device can be and/or is configured by way of the method according to at least one embodiment of the invention.

The method according to at least one embodiment of the invention can therefore be used universally in a corresponding system for medical data in order ideally to enable an optimization of the transmission performance of all of the communications links from first to second computing devices occurring therein to be performed. In this way an improvement of the overall performance of the system is achieved. For example, there can be provided on the corresponding first computing devices a program means, a software utility for example, which performs the measurements and calculations required in the method according to at least one embodiment of the invention. Needless to say, all statements made with regard to the method according to the invention can be applied analogously to the system according to at least one embodiment of the invention.

BRIEF DESCRIPTION OF THE DRAWINGS

Further advantages and specifics of the present invention will emerge from the example embodiments described below, as well as with reference to the drawing, in which:

The single FIGURE shows a detail from the system according to the invention comprising first and second computing devices.

DETAILED DESCRIPTION OF THE EXAMPLE EMBODIMENTS

Various example embodiments will now be described more fully with reference to the accompanying drawing in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figure.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The FIGURE shows a detail from the inventive system 1, in this case specifically a first computing device 2, for example a computer at a diagnostics workstation which transmits and/or receives medical image datasets to and/or from second computing devices 4 via communications links 3.

The second computing devices 4, of which three to thirty, for example, may be present for each first computing device 2, can be part, for example, of imaging devices 5, part of an archive computer 6 (in a PACS (Picture Archiving and Communication System) for example), or simply computing devices 4 of a workstation 7. Other types of second computing devices 4 are, of course, also conceivable. The essential point is that the second computing devices 4 can differ in terms of their communications characteristics, some of which are permanently predefined.

Image datasets are transmitted within the system 1 by way of the DICOM protocol. This means that the transmission performance of the communications links 3 is determined not only by way of the TCP/IP packet sizes (typically two parameters, one for sending, one for receiving), but also by way of the DICOM PDUs (DICOM processing data units). An optimization of the configuration of the communications links 3 for a set of configuration parameters composed of said four parameters is described in this exemplary embodiment, though, of course, other relevant configuration parameters can also be considered.

The method according to the invention is realized in the exemplary embodiment by way of a software utility 8 which is provided on the first computing device 2. The software utility 8 is also used during the installation of the first computing device 2. It serves for optimizing communications links 3 to the second computing devices 4 for the transmission of medical image datasets by way of the DICOM protocol. An optimization method is used for that purpose in the present case, with use being made of a multidimensional matrix, each of whose columns is formed by discrete, monotonously increasing values of a communication parameter. For example, seven to eight possible discrete values can be provided for each of the four configuration parameters.

The transmission performance is now determined for each set of configuration parameters resulting from the matrix by measuring the characterizing measurement values during the transmission of a sample packet or, as the case may be, sample dataset in the DICOM protocol. For example, transmission rate, transmission duration and resource utilization of the first and second computing device 2, 4, respectively, can be considered. A value for the transmission performance can be determined therefrom, for example by weighting a plurality of measurement values. The set of configuration parameters that has the best transmission performance is used for configuring the examined communications link 3. This set of communication parameters 3 is consequently stored.

Let it be pointed out that the optimization method can, of course, also be executed differently, in particular also when more predetermined values are specified or even when the configuration parameters are to be considered continuously. For example, methods are conceivable that incrementally restrict the region in which a search for the best transmission performance is conducted, or the like.

In this way it is possible by way of automatically performed measurements and an automatic evaluation to configure the communications links 3 such that an optimal transmission of medical data in the form of medical image datasets can take place via the communications link 3.

In this embodiment variant of the method according to an embodiment of the invention it is additionally provided that the determined configuration parameter datasets are transmitted to a database 9 which can be part of the system 1 or else can also be provided externally. Also stored in said database together with the selected sets of configuration parameters 9 is information from which the type of the corresponding second computing device 4 can be deduced, i.e. in particular specifications of the second computing device such as type/model, equipment level data and the like, ultimately all of the data that is relevant to the optimization of the communications link 3. It can then namely be provided that if a communications link 3 is to be configured from a first computing device 2 to a second computing device 4 that is already known in the database, then the set of configuration parameters can simply be retrieved from the database 9 again and used without a new measurement by the software utility 8 being necessary. These database functionalities can, of course, be implemented in addition in the software utility 8.

It goes without saying that the software utility 8 can also be used further following the installation of the first computing device 2. On the one hand it can be provided, for example, that the communications link 3 is reconfigured if something on a second computing device 4 has been modified. For that purpose a control element "Reconfigure" assigned to the communications link 3 or the second computing device 4 can be provided for example in a corresponding menu or in a corresponding visualization. Actuating the control element causes a new measurement and configuration to be initiated.

If a new second computing device 4 with which the first computing device 2 is to exchange medical data via a communications link 3 by means of the DICOM protocol is configured, the user is asked whether he or she wants an automatic configuration of the communications link 3 to be performed by means of the method according to an embodiment of the invention. If the user confirms this, the configuration is performed automatically. It can, of course, also be provided that such a user prompt will be avoided and the configuration performed fully automatically with knowledge of the new second computing device 4.

Further configuration parameters which can be taken into account, for example, in other embodiment variants of the inventive method or inventive system 1 are parameters related, for example, to the cooperative interaction of a plurality of network cards (teaming) as well as to burst or bulk modes.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, non-transitory computer readable medium and non-transitory computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory storage medium or non-transitory computer readable medium, is adapted to store information and is adapted to interact with a data processing facility or computer device to execute the program of any of the above mentioned embodiments and/or to perform the method of any of the above mentioned embodiments.

The non-transitory computer readable medium or non-transitory storage medium may be a built-in medium installed inside a computer device main body or a removable non-transitory medium arranged so that it can be separated from the computer device main body. Examples of the built-in non-transitory medium include, but are not limited to, rewriteable non-volatile memories, such as ROMs and flash memories, and hard disks. Examples of the removable non-transitory medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE SIGNS

1 System
2 Computing device
3 Communications link
4 Computing device
5 Imaging device
6 Archiving computer
7 Workstation
8 Software utility
9 Database

What is claimed is:

1. A method for configuring at least one communications link prior to transmission of medical image datasets over the communications link by way of a special transmission protocol from a first computing device to at least one second computing device, the method comprising:
    determining transmission performance automatically at the first computing device for a plurality of sets of configuration parameters of the communications link, the configuration parameters including at least one of a packet size, bulk modes and burst modes associated with the transmission over the communications link, the sets of configuration parameters being arranged in a multi-dimensional matrix, each column vector of the matrix having monotonously increasing entries contains values for one of the configuration parameters, with measurements being performed to determine the transmission performance of different ones of the sets of configuration parameters, the determining transmission performance including,
        transmitting sample packets over the communication link between the first computing device and the at least one second computing device using different ones of the sets of configuration parameters at a time of installation of the first computing device, and
        measuring the transmission performance of the transmitted sample packets, the sample packets being transmitted over the communication link prior to transmission of the medical image datasets; and
    selecting the set, of the plurality of sets of configuration parameters, determined to have a relatively best transmission performance, for the configuration of the at least one communications link to utilize when subsequently transmitting the medical image datasets over the communications link between the first computing device and the at least one second computing device, the selected set of configuration parameters containing a plurality of discrete values for the configuration parameters that collectively represents a relative best transmission performance among the sets of configuration parameters.

2. The method as claimed in claim 1, wherein, when a second computing device with which the first computing device is to communicate is added, the corresponding computing device is configured automatically, wherein at least one of an appropriate following confirmation by a user and an automatic reconfiguration of a communications link is initiated by a user.

3. The method as claimed in claim 1, wherein a selected set of configuration parameters is stored in a database together with at least one of a type of the second computing device and equipment level data of the second computing device.

4. The method as claimed in claim 3, wherein the set of configuration parameters stored in the database is retrieved and used for configuring a communications link to a second computing device that in terms of at least one of the type and equipment level data matches a second computing device that is stored in the database.

5. A system for at least one of managing and processing medical image datasets via a plurality of computing devices, the system comprising:
at least one communications link for transmitting medical image datasets over the communication link by way of a special transmission protocol from a first one of the plurality of computing devices to at least one second one of the plurality of computing devices, the system being configured to
determine, prior to transmission of the medical image datasets, transmission performance automatically at the first computing device for a plurality of sets of configuration parameters of the communications link, the configuration parameters including at least one of a packet size, bulk modes and burst modes associated with the transmission over the communications link, the sets of configuration parameters being arranged in a multi-dimensional matrix, each column vector of the matrix having monotonously increasing entries contains values for one of the configuration parameters, with measurements being performed to determine the transmission performance of different ones of the sets of configuration parameters, the determining transmission performance including,
transmitting sample packets over the communication link between the first computing device and the at least one second computing device using different ones of the sets of configuration parameters at a time of installation of the first computing device, and
measuring the transmission performance of the transmitted sample packets, the sample packets being transmitted over the communication link prior to transmission of the medical image datasets, and
select the set, of the plurality of sets of configuration parameters, determined to have a relatively best transmission performance, for the configuration of the at least one communications link to utilize when subsequently transmitting the medical image datasets over the communications link between the first computing device and the at least one second computing device, the selected set of configuration parameters containing a plurality of discrete values for the configuration parameters that collectively represents a relative best transmission performance among the sets of configuration parameters.

6. The method as claimed in claim 1, wherein an optimization method is used for determining a set of configuration parameters having the best transmission performance.

7. The method as claimed in claim 1, wherein the special transmission protocol is a DICOM protocol, and wherein the at least one second computing device includes a plurality of different second computing devices.

8. The method as claimed in claim 2, wherein at least one of an appropriate following confirmation by a user and an automatic reconfiguration of a communications link is initiated by a user is achieved by actuating a control element.

9. A non-transitory computer readable medium including program segments for, when executed on a computer device, causing the computer device to implement the method of claim 1.

10. The system as claimed in claim 5, wherein the special transmission protocol is a DICOM protocol, and wherein the at least one second computing device includes a plurality of different second computing devices.

11. The method of claim 1, wherein the sets of configuration parameters are arranged in the matrix such that each set of configuration parameters represents a column or row thereof.

12. The system of claim 5, wherein the sets of configuration parameters are arranged in the matrix such that each set of configuration parameters represents a column or row thereof.

* * * * *